United States Patent [19]
Besnier

[11] Patent Number: 5,533,407
[45] Date of Patent: Jul. 9, 1996

[54] ASSEMBLY FOR TAKING LIQUID SAMPLES IN JUGS SEALED BY SCREW GAPS

[75] Inventor: Joseph Besnier, Acqueville, France

[73] Assignee: Compagnie Generale Des Matieres Nucleaires, Velizy-Villacoublay, France

[21] Appl. No.: 312,287

[22] Filed: Sep. 26, 1994

[30] Foreign Application Priority Data

Oct. 14, 1993 [FR] France ..................... 93 12216

[51] Int. Cl.$^6$ .............. G01N 35/10; B67B 7/18
[52] U.S. Cl. ............... 73/864.25; 73/864.31; 73/863.81
[58] Field of Search .............. 73/864.25, 865.81, 73/863.85, 864.23, 864.24, 864.31

[56] References Cited

U.S. PATENT DOCUMENTS

| | | | |
|---|---|---|---|
| 2,571,302 | 10/1951 | Smith . | |
| 4,478,095 | 10/1984 | Bradley et al. | 73/864.23 X |
| 4,526,045 | 7/1985 | Reekie | 73/864.31 |
| 4,616,515 | 10/1986 | Dancoine | 73/864.31 |

FOREIGN PATENT DOCUMENTS

| | | |
|---|---|---|
| 0557828 | 9/1993 | European Pat. Off. . |
| 1250479 | 12/1960 | France . |
| 1602189 | 11/1970 | France . |
| 878504 | 10/1961 | United Kingdom . |
| 913022 | 12/1962 | United Kingdom . |

OTHER PUBLICATIONS

Patent Abstracts of Japan; Grp. M1196; vol. 15, No. 513; ABS–Pub. Date Dec. 26, 1991 (3-226484) "Cap Opening and Closing Device".
Patent Abstracts of Japan, vol. 15, No. 513 (M–1196) 26 Dec. 1991 & JP 03 326 485 (Shimadzu Corp.)

Primary Examiner—Thomas P. Noland
Attorney, Agent, or Firm—Pearne, Gordon, McCoy & Granger

[57] ABSTRACT

In order to automatically take samples of radioactive liquids contained in jugs (14) sealed by screw caps, an assembly is proposed which consists of a gripping module (20) for gripping and holding the jug, a module (22) for opening and closing the jugs, and a sampling module (24). The gripping module (20) brings each jug in from of the opening and closing module (20) and fulfils a holding function during the screwing and unscrewing of the cap or plug and during the sampling operation or operations. The sampling module (24) carries out the sampling operations by means of an end piece (138) for the suction and transfer of the liquid into a container (26) for analysis purposes.

10 Claims, 5 Drawing Sheets

ASSEMBLY FOR TAKING LIQUID SAMPLES IN JUGS SEALED BY SCREW GAPS

BACKGROUND OF THE INVENTION

The invention relates to an assembly for remotely and, in an automated manner, taking liquid samples contained in jugs sealed by screw caps or plugs.

The assembly for taking liquid samples according to the invention can, in particular, be used within a tight cell for the analysis of chemical products such as radioactive products moved into said cell in tight jugs. More specifically, the tight cell containing the sampling assembly according to the invention can form part of an automated installation like that described in FR-A-2 675 582. In such an installation, liquid products are sampled in automated manner at different points of a production or processing line and introduced into tight jugs, which are then automatically transferred into analysis units by pneumatic transfer circuits.

In such an installation, the jugs containing the samples to be analyzed drop directly into the bottom of the analysis units. Prior to carrying out the analytical preparation of the samples contained in the jugs, it is consequently necessary for the operators to manually perform, with the aid of handling grippers, three successive manual operations consisting of gripping of a jug, opening the jug then taking a sample from the jug in question. This leads to a certain number of problems which will now be described.

The manual gripping of a jug by the operator with the aid of handling grippers makes it necessary for the operator to search for the jug in the bottom of the analysis unit identifying it by reading a code carried on each jug. In view of the fact that the jugs are loose on the analysis unit bottom, this operation is tedious and difficult. It is further complicated by the optical deformations caused by the inspection window through which the operator reads the codes carried on the jugs. This leads to an error risk and even to the loss of certain jugs, which can lead to the operator requesting a new sampling operation and consequently increases the amount of waste.

In order to open a previously grasped jug, the operator must use two handling grippers. Apart from the difficult nature of this operation, there is a serious contamination risk with respect to the jug content by the grippers and vice versa. In addition and in even more serious manner, the jug opening operation leads to a serious risk of overturning its content in the bottom of the analysis unit. This makes it necessary to call for another jug and leads to an unacceptable time loss. Moreover, the jug content is then directly discharged into the liquid effluents, which is prejudicial to the desired limitations on such effluents.

It should also be noted that the use of handling grippers makes it impossible to seal the jugs, so that the surplus samples not used for the analysis and remaining in the bottom of the jugs constitute waste and cannot be recycled.

Finally, the third operation manually performed by the operator consists of taking a liquid sample from the jug with the aid of a conventional pipette connected by a pipe to a burette located outside the analysis unit. A first disadvantage linked with this operation results from the fact that the operator must read a calibration mark carried on the pipette, which makes it necessary for said operator to be present and represents a long and difficult operation. A second disadvantage is the risk, due to an unsatisfactory manipulation, of passing radioactive liquid to be analyzed outside the analysis unit and into the immediate vicinity of the operator's head.

SUMMARY OF THE INVENTION

The invention relates to an assembly for taking liquid samples permitting the remote, automated performance of gripping and opening operations with respect to jugs, as well as the operation of taking a sample from a jug, which eliminates risks of errors, handling difficulties and time losses of the existing manual procedure and limits effluents to the absolute minimum.

According to the invention, an assembly for taking liquid samples from jugs sealed by screw caps includes:

- a module for gripping the jugs having a gripper able to hold a jug in accordance with a substantially vertical axis, gripper opening and closing control means, and control means for a horizontal displacement of the gripper between a gripping station and an opening station for the jugs;
- a module for opening and closing the jugs positioned to the right of the jug opening station, which has nippers with vertical axes, means for the control of the tightening and loosening of the nippers, means for the control of the rotation of the nippers about the vertical axis thereof and means for the control of a vertical displacement of the nippers; and
- a module for sampling liquid incorporating a suction end-piece, which has a substantially vertical axes, means for the control of the horizontal displacement of the endpiece between a sampling position, in which the vertical axes of the nippers and the suction endpiece coincide, and a position for the distribution of the liquid sampled in a receptacle, and means for the control of the vertical displacement of the suction endpiece.

In such an assembly, the jug in which it is wished to carry out a sampling operation is gripped by the gripping module gripper and maintained by gripping module while the jug's cap or plug is unscrewed by the opening and closing module and then while sampling is carried out by means of the sampling module. The jug can then be resealed by the opening and closing module before being brought by the gripping module to a ramp making it possible to transfer it out of the analysis unit, e.g. into a unit permitting the recycling of the unused part of liquid samples still present in the jugs. All the aforementioned disadvantages associated with the use of handling grippers for ensuring the gripping and opening of the jugs and then the taking of the samples are eliminated by the use of such an assembly. In particular, the liquid and solid effluents are minimized and the risks of error in the measurements and handling operations are eliminated.

It should be noted that the use of three separate modules, controlled by the same automaton, makes it possible to install the assembly on existing analysis units, which would not be the case with a robot fulfilling the three functions.

In a preferred embodiment of the invention, the gripper is installed at a bottom end of a rotary shaft with a vertical axis, displaced with respect to the axis of the jug held by the gripper and the control means of a horizontal displacement of the gripper incorporating means for controlling a rotation of the rotary shaft.

Each jug can be introduced into the gripper by an upper jug supply chute when the gripper is in the open position. The dropping of the jug into the chute is then interrupted by a retractable base associated with the gripping module and which is placed below the gripper, above a lower jug discharge chute.

The gripping module can also comprise means for locking the gripper in position in front of the gripping station and the jug opening station.

In the preferred embodiment of the invention, the opening and closing module comprises a pin having a vertical axis and connecting the nippers to rotation control means, and a rod positioned coaxially within the pin and connecting the nippers to the tightening and loosening control means.

Advantageously, the opening and closing module also comprises a retractable drop collecting plate, which can be positioned below the nippers in order to collect a sample droplet which may drop from the cap when the cap has been unscrewed from the jug.

In the latter case, the means for controlling a vertical displacement of the nippers act simultaneously on the drop collecting plate, in such a way that the drop collecting plate is placed below the nippers when the nippers do not occupy a bottom screwing and unscrewing position.

In the preferred embodiment of the invention, the suction endpiece is mounted on a rotary, horizontal arm, whose rotation is controlled by the means for controlling a horizontal displacement of the endpiece.

Preferably, so as to ensure that no contamination passes outside the analysis unit, the suction endpiece is connected to a hydraulic safety guard located within the said unit.

BRIEF DESCRIPTION OF THE DRAWINGS

The invention is described in greater detail hereinafter relative to a non-limitative, preferred embodiment and with reference to the attached drawings, wherein show:

FIG. 4 A sectional view along line IV—IV of FIG. 3.

DETAILED DESCRIPTION OF THE PREFERRED EMBODIMENT

Figure 1:
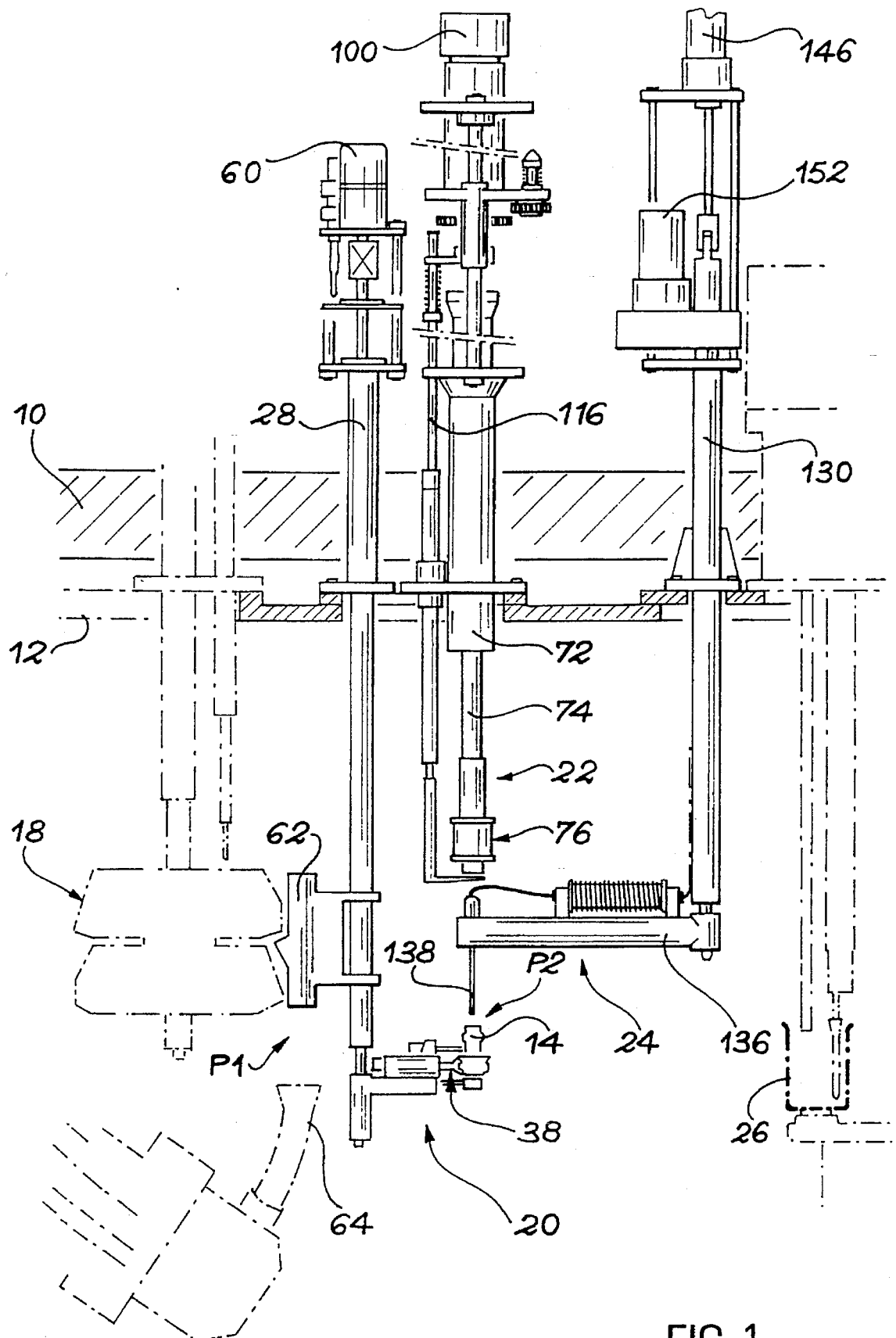
FIG. 1 A side view diagrammatically showing a liquid sample taking assembly according to the invention.

The sampling assembly diagrammatically illustrated in FIG. 1 is intended to be associated with an analysis unit in which one or more chemical analyses are to be carried out on radioactive liquid products taken beforehand at different points of a production or reprocessing line. In order to be transferred into the analysis unit, the radioactive liquid product sampled on the production or reprocessing line are introduced into jugs, which are moved up to the analysis unit by a pneumatic transfer circuit, e.g. as described in FR-A-2 675 582. The sampling and transfer of the liquid products to be analyzed does not form part of the invention and no description thereof will be provided here. The sampling assembly according to the invention serves to grasp in turn each of the jugs in which one or more liquid samples are to be taken for analysis purposes, followed by opening the said jug by unscrewing the screw cap or plug, performing in the open jug the intended sampling operations, resealing the jug so as to permit its redispatch to the outside of the analysis unit. The sampling assembly performs these different operations with the aid of motor means permitting a complete automation.

When they enter the analysis unit, the jugs are advantageously stored in an appropriate device not forming part of the invention and consequently not described. If this is made possible by the speed and order of the passage of the jugs in the analysis unit, the jugs can also be taken up directly by the sampling assembly according to the invention, as soon as they enter the analysis unit.

In FIG. 1, reference numeral 10 designates part of the upper, horizontal wall of the analysis unit, which is internally duplicated by a metal skin 12. The jugs 14 containing the radioactive products to be analyzed are introduced into the analysis unit by a not shown vertical tube, which passes through the wall 10 and the skin 12. In the embodiment diagrammatically illustrated in FIG. 1, the jugs 14 are then placed in a buffer storage device, whereof only the contour is represented at 18.

According to the invention, the liquid sampling unit comprises three separate modules supported by the metal skin 12, which internally duplicates the upper, horizontal wall 10 of the analysis unit. These three modules consist of a jug gripping module 20, a jug opening and closing module 22 and a module 24 for sampling liquid in the jugs. Each of these modules is designed in such a way that the actuators and sensors are largely placed outside the analysis unit. This feature facilitates maintenance and limits the overall dimensions of the assembly within the analysis unit and decreases the numbers of actuators and sensors disposed of as waste.

The jug gripping module 20 has the first function of gripping the jug when it leaves the buffer storage device 18 or directly when it enters the analysis unit if such a storage device is not provided. This applies with respect to each jug 14 in which one or more liquid samples are to be taken for analysis purposes. The jug gripping module 20 also has the function of transferring the jug which it has just grasped to the right of the jug opening station materialized by the opening and closing module 22. It then holds the jug during the operation of the opening and closing module 22, and then when a sample is taken in the jug with the aid of the liquid sampling module 24. Finally, when the sampling operations have been carried out, the jug gripping module 20 continues to hold the jug so as to permit its closure by the opening and closing module 22 and then ensures the transfer of the resealed jug to a station for dispatching the jug to the exterior of the analysis unit.

The functions of the jug opening and closing module 22 are the unscrewing of a screw cap 16 (FIG. 2), which seals the jug 14 grasped by the gripping module 20, and then the screwing up again of the same cap when the sampling operation or operations have been carried out by the liquid sampling module 24.

Finally, the liquid sampling module 24 has the function of sucking or driving one or more liquid samples out of the jug held by the gripping module 20 and transferring same into one or more containers 26 positioned inside the analysis unit, so that chemical analyzes can be carried out.

A preferred embodiment of the jug gripping module 20 will now be described in greater detail relative to FIGS. 2 to 4.

The jug gripping module 20 comprises a support sleeve 28 with a vertical axes, which traverses the horizontal, upper wall 10 of the analysis unit, as well as its metal skin 12. In its central portion, the support sleeve 28 has a flange 30 by which it is fixed, e.g. by means of screws 32, to the metal skin 12.

A axis, rotary shaft 34 with a vertical axis is mounted in the support sleeve 28 so as to be able to freely rotate therein, while being immobilized there in translation. Not shown gaskets or seals are placed between the rotary shaft 34 and the support sleeve 28 in order to maintain the confinement.

At its lower end located within the analysis unit, the rotary shaft 34 projects out of the support sleeve 28 and carries a preferably interchangeable, gripper support 36. The gripper support 36 is in the form of a horizontal arm at the end of which projects a gripper 38 able to grip a jug 14 in accordance with a vertically axis displaced with respect to the vertical axis of the rotary shaft 34. More specifically, the gripper 38 comprises two circular arc jaws 40 having a vertical axis of symmetry coinciding with the axis of a jug 14 gripped between the jaws 40.

Figure 2:
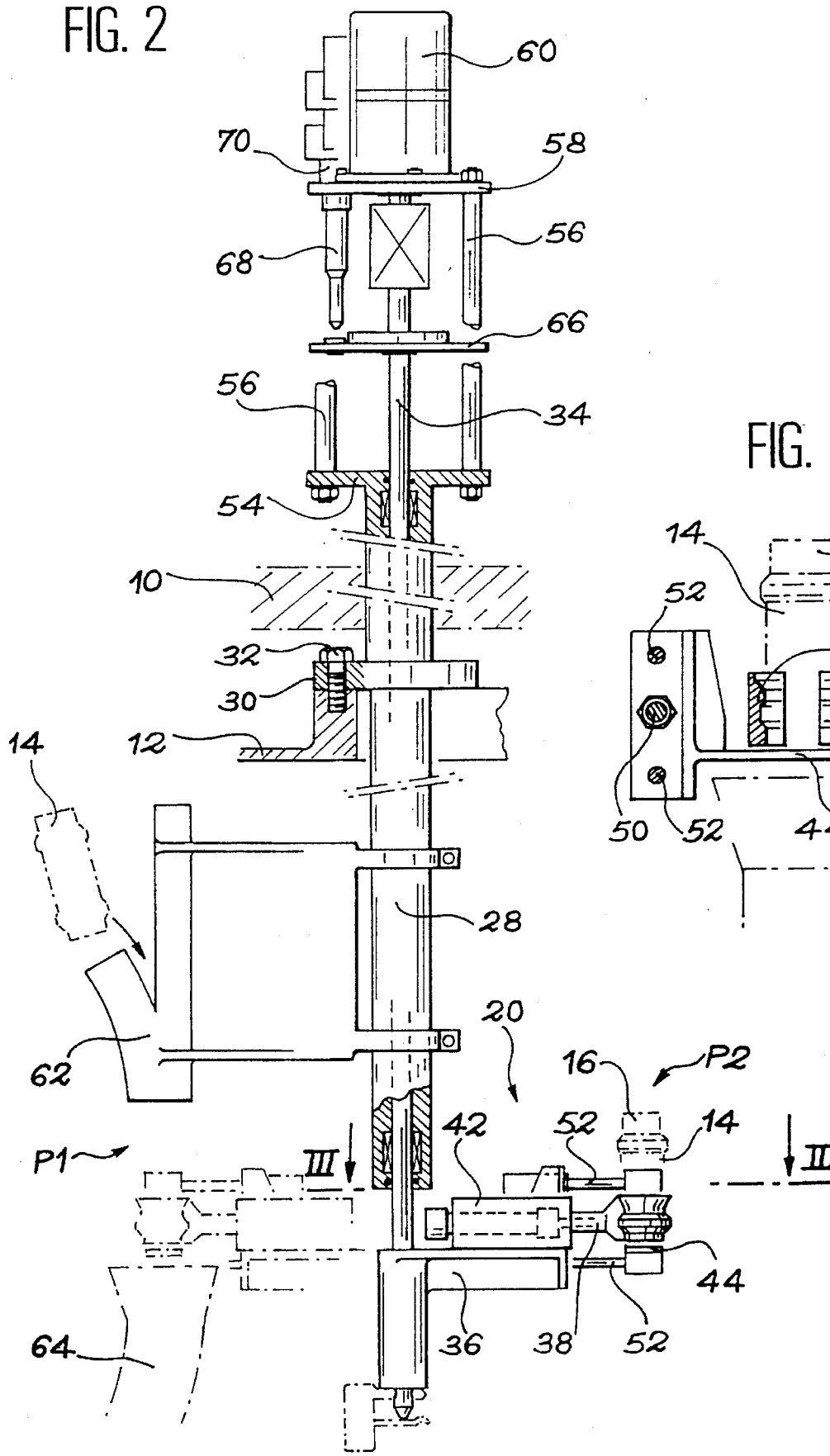
FIG. 2 A vertical sectional view showing on a larger scale the jug gripping module used in the assembly of FIG. 1.
Figure 3:
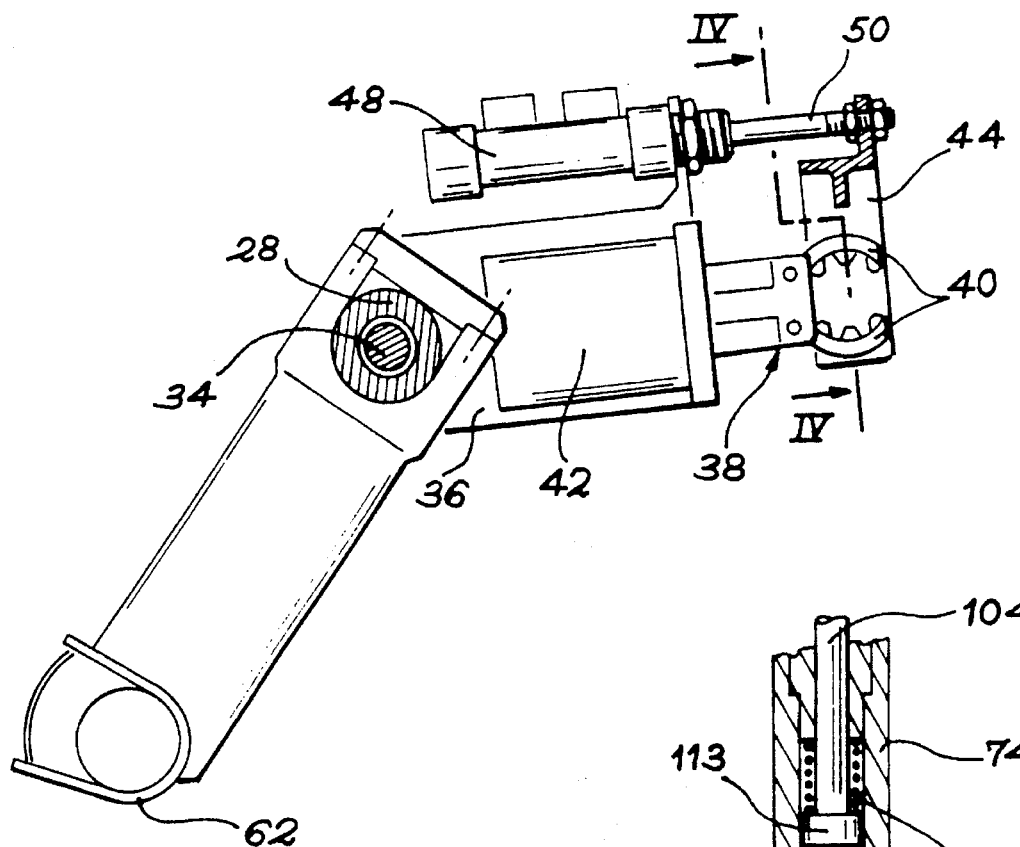
FIG. 3 A sectional view along line III—III of FIG. 2 illustrating on a larger scale the lower portion of the gripping module.

In the embodiment illustrated in FIGS. 2 to 4, the two jaws 40 of the gripper 38 are mobile and articulated in symmetrical manner with respect to a plane passing both through their vertical symmetry axis and through the vertical axis of the rotary shaft 34. The movement of the jaws 40 is controlled by a jack 42 mounted on the gripper support 36.

As is more specifically illustrated in FIGS. 3 and 4, the gripper support 36 also carries a retractable base 44 normally positioned below the gripper 38 and below a jug 14 possibly held in the gripper.

More specifically, the gripper support 36 laterally carries a jack 48 (FIG. 3), whose rod 50 supports the retractable base 44 at its end. Thus, the actuation of the jack 48 controls a translational movement of the retractable base 44 parallel to the horizontal axis of the jack 42 between the active position illustrated in continuous line form in FIGS. 2 to 4 and a retracted position in which the base 44 is displaced towards the gripper support 36 with respect to the gripper 38. Two rods 52 (FIGS. 2 and 4) are fixed to the base 44, respectively above and below the rod 50 of the jack 48, and slide in guide sheaths integral with the gripper support 36, so as to prevent any rotation of the retractable base 44 about the rod 50 and maintain the base 44 horizontal.

The upper end of the support sleeve 28 within the analysis unit carries a lower, horizontal plate 54, which is connected by small vertical columns 56 to an upper, horizontal plate 58 carrying a geared motor 60 (FIGS. 1–2). The geared motor 60 rotates the rotary shaft 34, so as to angularly displace the gripper 38 about the vertical axis of the shaft 34 between a jug gripping and discharge station p1 and a jug opening station p2. It should be noted that the jug gripping and discharge stations, which coincide in the embodiment illustrated in the drawings, can also be located at separate points.

The jug gripping station is materialized by an upper jug supply chute 62 with a vertical axis below which is placed the gripper 38 equipped with its detachable base 44. In the embodiment illustrated in FIGS. 2 and 3, the upper chute 62 is directly fixed to the support sleeve 28, which ensures a satisfactory alignment of the gripper below the chute 62 in the gripping position.

In the embodiment illustrated in the drawings, the jug 14 to be treated drops into the upper chute 62 from the buffer storage device 18. As a variant, the upper chute 62 can also directly receive a jug coming from the outside of the analysis unit.

The jug discharge station is materialized by a lower jug discharge chute 64 having a vertical axis and above which is located the gripper 38 when occupying its jug discharge position. In the illustrated embodiment, the vertical axes of the lower chute 64 and the upper chute 62 coincide.

When the gripper 38 is placed in front of the jug opening and closing station, where the liquid sampling operations also take place, the vertical axis of the gripper coincides with the vertical axis of the opening and closing module 22, whereof a detailed description will be given hereinafter.

In order to avoid any handling error, the gripping module 20 illustrated in FIG. 2 is equipped with a device for locking the gripper 38 to the right of the gripping and discharge station, as well as to the right of the jug opening and closing station The actuation of the locking device conditions the putting into operation of the jacks 42, 48.

In the embodiment illustrated in FIG. 2, the locking device comprises a disk 66 integral with the rotary shaft 34 between the plates 54 and 58. This disk 66 has two not shown holes equidistant of the axis of the shaft 34 and angularly displaced about said axis. The locking device also comprises a vertical locking finger 68 which can be displaced in accordance with its axis between an upper position and a lower position under the action of a jack 70 mounted on the upper plate 58. In its upper position illustrated in FIG. 2, the locking finger 68 is entirely positioned above the disk 66, whereas it traverses one or other of the holes formed in said disk when it occupies its lower position. More specifically, the holes formed in the disk 66 are positioned in such a way that one of them is located vertically of the locking finger 68 when the gripper 38 is to the right of the gripping and discharge station and the other hole is positioned vertically of the locking finger 68 when the gripper 38 is to the right of the jug opening and closing station.

Not shown, end of travel sensors are associated with the jacks 42, 48 and 70, as well as the geared motor 60, in order to control their automatic stopping when the desired displacement has taken place.

It should be noted that in a not shown variant, the jacks 42 and 48 are advantageously replaced by motors positioned outside the analysis unit and controlling the corresponding movements of the gripper 38 and, the detachable base 44 via appropriate mechanisms, e.g. of the rack and pinion type. The transmission of the movements through the wall 10 of the analysis unit then takes place by one or more vertical rods. A preferred embodiment of the module 22 for opening and closing the jugs 14 will now be described in greater detail relative to FIGS. 5 and 6. This jug opening and closing module 22 firstly comprises a vertically axed, support sleeve 72, which passes through the horizontal wall 10 and the metal skin 12 of the analysis unit. More specifically, the sleeve 72 has a collar 73, which is fixed to the metal skin 12, e.g. by not shown screws.

A hollow pin 74 with a vertical axis is fitted in the sleeve 72 so as to be able to rotate and slide freely within the latter. Not shown seals are provided between the pin 74 and the sleeve 72 in order to maintain the confinement of the analysis unit. At its lower end, the hollow pin 74 carries nippers 76 to be described in greater detail hereinafter relative to FIG. 6.

The hollow pin 74 projects above the upper end of the support sleeve 72 and traverses a lower, horizontal plate 78, so as to be able to rotate freely within said plate, while being immobilized in translation with respect thereto. The lower, horizontal plate 78 slides on small vertical columns 80, whereof the lower end is fixed to a flange 82 integral with the support sleeve 72.

The upper ends of the columns 80 carry an upper, horizontal plate 84. A jack 86 is fixed to the lower, horizontal plate 78 and its control rod 87 projects vertically downwards in order to be fixed by its lower end to the flange 82. This arrangement enables the jack 86 to control a vertical displacement of the nippers 76 between an upper and a lower position.

Below the lower, horizontal plate 78, the hollow pin 74 carries a pinion 88 used for controlling the rotation of the pin. The control of this rotary movement is ensured either by a stepping motor, or by a normal motor associated with a not shown, mechanical coder.

On its upper face, the lower, horizontal plate 78 carries a tubular body 96, whose vertical axis coincides with the axis of the support sleeve 72 and the hollow pin 74. At its upper end, the tubular body 96 carries an upper, horizontal plate 98 on which is mounted a geared motor 10. The output shaft of the geared motor 100 rotates, by means of a torque limiter 102, a cylindrical rod 104, which coaxially traverses the hollow pin 74, so as to control the actuation of the nippers 76 by its lower end.

Figure 6:
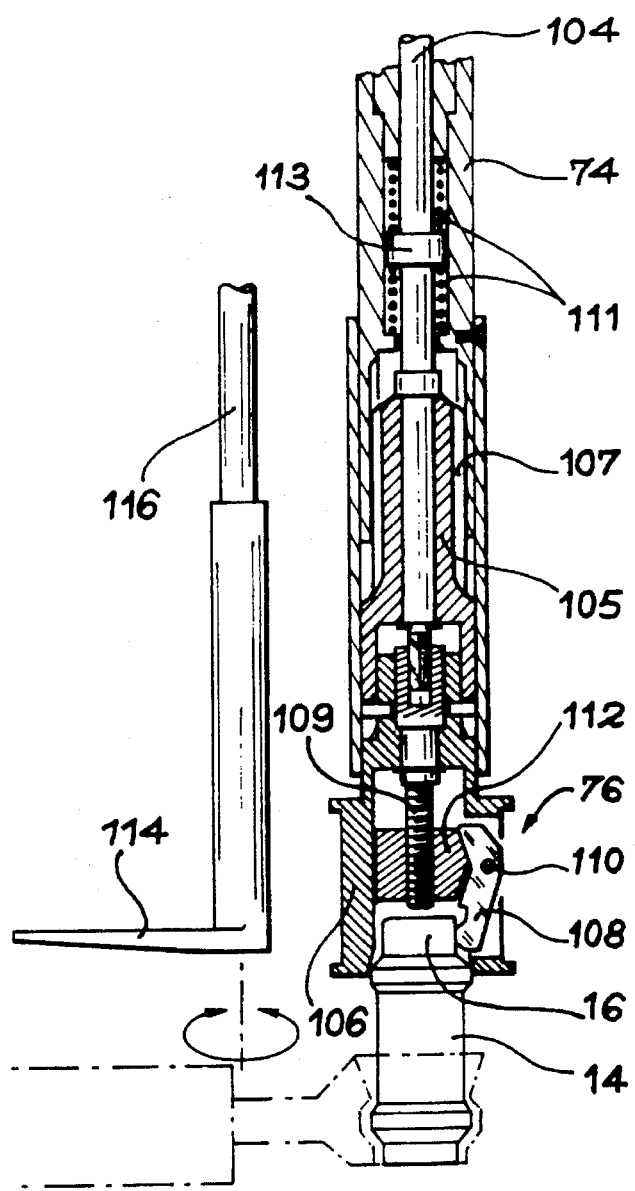
FIG. 6 A side view in longitudinal section illustrating on a larger scale the lower end of the jug opening and closing module.

As is more specifically illustrated by FIG. 6, the nippers 76 have a tubular endpiece 106 fitted in detachable manner at the lower end of a nipper holder 105, which is itself connected in translation to the lower end of the rod 104 and connected in rotation to the hollow pin 74, e.g. by means of keys 107. In its lower part, the tubular endpiece 106 carries three tightening or locking noses 108 (whereof only one is visible in FIG. 6) arranged so as to be able to pivot about three horizontal axes 110, or oriented in three orthogonal directions with respect to the vertical common axis of the pin 74 and the rod 104. The three tightening noses 108 are positioned at 120° from one another around said vertical axis, so that their lower ends form the nippers 76 in which can be locked the screw cap 16 of a jug 14.

A yoke 112 is trapped between the noses 108, level with the axes 110, so as to be in contact with a V-shaped indentation formed on each of the noses. The contact surfaces of the yoke 112 and the tightening noses 108 are such that an upward or downward displacement of the yoke 112 respectively has the effect of pivoting the noses 108 in the tightening or loosening direction of the nippers 76. These contact surfaces also have the effect of immobilizing in rotation the yoke 112 within said tubular endpiece 106.

At its lower end, the rod 104 rotates a threaded rod 109 mounted in the endpiece 106 and to which is screwed the yoke 112. Consequently a rotation of the rod 104 in one or other direction, controlled by the geared motor 100, has the effect of raising or lowering the yoke 112 in the tubular endpiece 106 and consequently tightening or loosening the nippers 76.

As is also illustrated in FIG. 6, the rod 104 has a predetermined vertical clearance within the hollow pin 74, with respect to a central position determined by the action of two compression springs 111 placed above or below a shoulder 113 formed on the rod 104 and bearing on shoulders formed in the pin 74.

This feature authorizes a slight displacement of the nippers 76, linked in translation with the rod 104, in the upwards or downwards direction with respect to the hollow pin 74. When the latter is rotated in order to ensure the screwing or unscrewing of the cap 16, the downward or upward displacement of the nippers 76 resulting from said action is consequently rendered possible.

Figure 5:
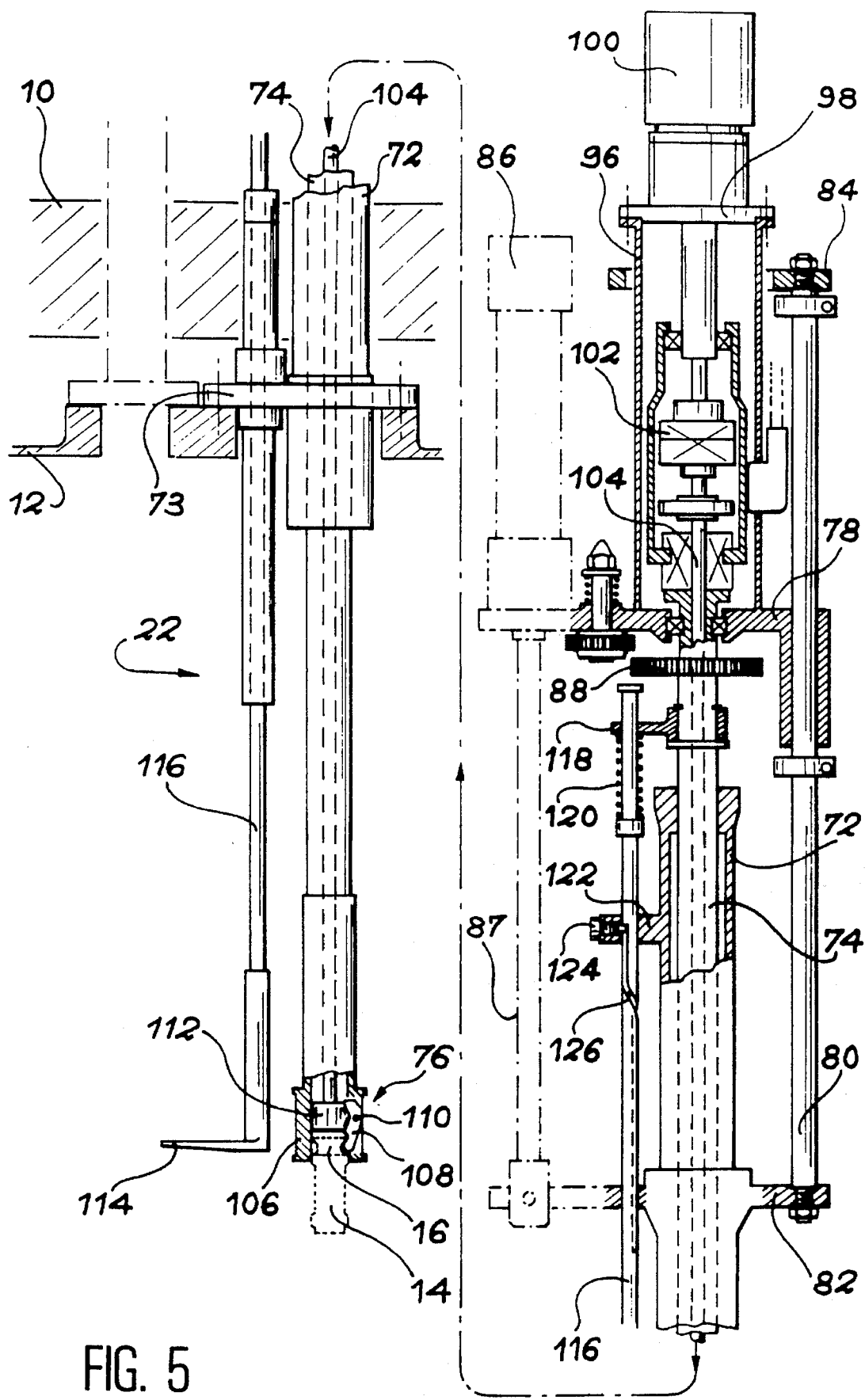
FIG. 5 A sectional view in part longitudinal section, the right and left parts respectively representing the upper and lower portions of the jug opening and closing module.

As is also illustrated by FIGS. 5 and 6, the module 22 for opening and closing the jugs 14 also comprises a retractable, horizontal drop collecting plate 114 for being automatically positioned below the nippers 76 when the latter move from the lower position illustrated in the drawings and in which screwing and unscrewing take place.

More specifically, the drop collecting plate 114 is installed at the lower end of a rotary, vertical rod 116, which passes through the flange 73 in such a way as to be able to rotate and slide therein. This passage is tight in order to maintain the confinement of the analysis unit. At its upper end, located beyond the analysis unit, the rod 116 traverses an arm 118 linked in translation with the hollow pin 74, but in which the latter can freely rotate. More specifically, the arm 118 is positioned between two shoulders formed on the rod 116, so that the latter has a certain vertical clearance with respect to the arm 118. A compression spring 120 is placed between the arm 118 and the lower shoulder of the rod 116, so as to normally maintain the latter in a relatively low position with respect to the arm 118.

Below the arm 118, the rod 116 also traverses an arm 122 integral with the support sleeve 72. A teat screw 124, whose end penetrates a groove 126 formed on the rod 116 is fixed to the arm 122. The groove 126 has an upper portion of limited length which is oriented vertically, a lower portion of greater length which is also vertically oriented and an oblique intermediate portion linking the upper and lower portions. This arrangement has the effect of bringing about an automatic rotation of the rod 116 by a given angle about its vertical axis, when there is a relative vertical displacement between said rod and the support sleeve 72. The retractable drop collecting plate 114 is thus automatically offset with respect to the nippers 76, when the latter occupy their lower position illustrated in FIG. 5 and it is automatically placed below the nippers 76 as soon as the latter rise and move away from the lower screwing and unscrewing position for the cap 16.

More specifically, when the nippers 76 approach the lower position illustrated in FIG. 5, the teat screw 124 bears against the top of the groove 126. The end of the descent of the nippers 76 consequently has the effect of slightly moving the arm 118 away from the upper shoulder formed on the rod 116, whilst compressing the spring 120. This characteristic makes it possible to totally free the space located below the nippers 76, so as to prevent any interference with the gripping module 20.

A description of a more detailed nature will now be given relative to FIG. 7 of a preferred embodiment of the sampling module 24 of FIG. 1. This sampling module 24 comprises a vertically axed, support sleeve 130, which traverses the upper, horizontal wall 10 of the analysis unit and has a flange 132 by which it is fixed to the metal skin 12 internally duplicating the said wall.

The sleeve 130 supports a vertical shaft 134 which can be rotated about its axis and a translatory movement along said axis. Seals are provided in order to maintain the confinement of the analysis unit. At its lower end located in the analysis unit, the shaft 134 supports a horizontal arm 136, which carries at its end a suction endpiece 138 in the form of a vertical needle.

At its upper end located outside the analysis unit, the support sleeve 130 is integral with a lower, horizontal plate 140. This plate is connected by small vertical columns 142 to an upper, horizontal plate 144. The latter supports a jack 146, whose control rod 148 projects vertically downwards.

At its lower end, the control rod 148 of the jack 146 is fixed to a carriage 150 able to slide vertically along the columns 142. The upper end of the shaft 134 is supported in rotary manner in the carriage 150, whilst being integral therewith in translation. The carriage 150 supports a geared motor 152, whose vertical output shaft carries a pinion 154, which meshes with a pinion 156 integral with the shaft 134.

The arrangement described with reference to FIG. 7 makes it possible to control the rise and fall of the suction endpiece 138 by actuating the jack 146, as well as the rotation of the endpiece about the vertical axis of the shaft 134 by operating the geared motor 152.

The carriage 150 also supports a locking jack 158 able to displace a vertical locking rod 160 between an upper and a lower position. In its lower position, the locking rod 160 penetrates a not shown indentation formed in a horizontal disk 162 integral with the shaft 134. More specifically, the disk 162 has two indentations corresponding to two different angular positions of the suction endpiece 138, in which the latter occupies either a sampling position for which its vertical axis coincides with the axis of the nippers 76 of the jug opening and closing module 22, or one or more sampled liquid distribution positions, in which the suction endpiece 138 is positioned vertically of a container such as the container 26 in FIG. 1. When the locking rod 160 occupies its upper position, it is freed from the indentations formed in the disk 162.

Figure 7:
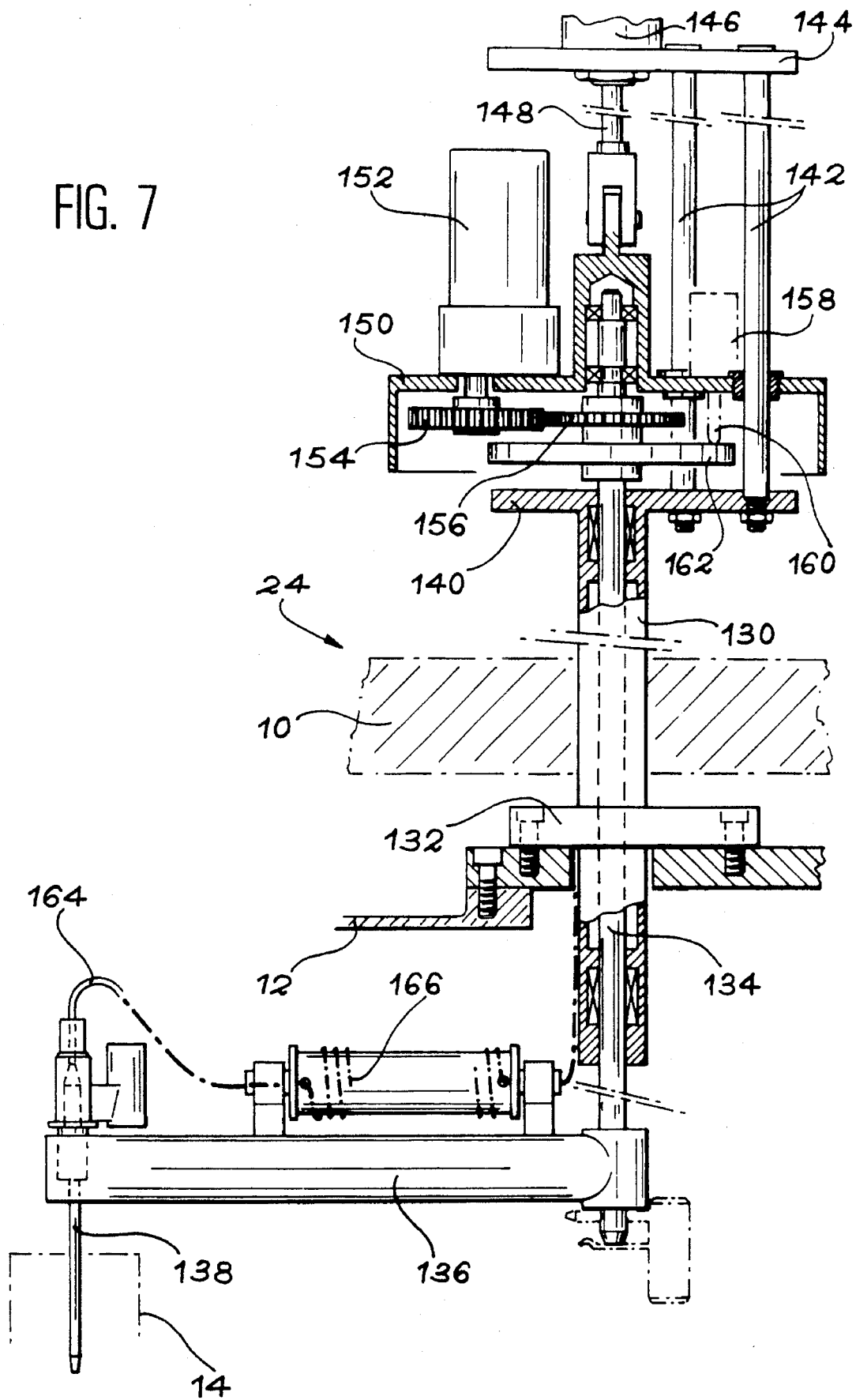
FIG. 7 A side view in part longitudinal section showing on a larger scale the sampling module used in the assembly of FIG. 1.

As is also illustrated in FIG. 7, the upper end of the suction endpiece 138 issues into a flexible tube 164, which passes through a safety hydraulic guard 166 before traversing the upper, horizontal wall 10 of the analysis unit in order to be connected to a not shown, suction piston or pump located outside said unit. The hydraulic safety guard 166 can either be directly mounted on the horizontal arm 136, as illustrated by FIG. 7, or on that part of the support sleeve 130 below the metal skin 12.

The use of the liquid sample taking assembly according to the invention will now be briefly described.

The jug 14 containing the sample to be analyzed drops into the chute 62 either from the storage device 18, or directly from the exterior of the analysis unit. The gripper 38 of the gripping module 20 is then open and the retractable base 44 is positioned vertically of said gripper. Consequently, the dropping of the jug 14 is stopped by the base 44. The jack 42 is then actuated in such a way that the jug 14 is grasped by the gripper 38.

The geared motor 60 for controlling the angular displacement of the gripper 38 about the vertical axis of the shaft 34 is then actuated, so as to position the jug 14 vertically of the opening and closing module 22. At this instant, it should be noted that the suction endpiece 138 of the sampling module 24 occupies its distribution position, i.e. it is angularly displaced with respect to the jug opening and closing module 22. Moreover, said module occupies its waiting position in which the nippers 76 are in the upper position.

When the axis of the jug 14 is aligned with that of the jug opening and closing module 22, the jack 86 is actuated so as to control the descent of the nippers 76. At the end of said descent, the drop collecting plate 114 is automatically retracted into the position shown in FIG. 5, so that the tubular endpiece 106 covers the top of the jug 14 held in the gripper 38. This is made possible by the fact that the nippers 76 are then open, i.e. the yoke 112 occupies its lower position within the endpiece 106.

As soon as the descent of the nippers 76 is at an end, the geared motor 100 is actuated in the tightening direction of the nippers 76, whose noses 108 then engage on the cap 16 of the jug 14, which remains secured in the gripper 38.

The opening of the jug 14 is then carried out by controlling the rotation of the hollow pin 74 and the nippers 76 mounted in the base of said pin, in the unscrewing direction of the cap 16. This unscrewing is accompanied by a rise of the rod 104 with respect to the hollow pin 74 by a distance authorized by a vertical clearance existing between the rod 104 and the hollow pin 74.

When the unscrewing of the cap 16 is at an end, the jack 86 is again actuated in the sense of raising the nippers 76. During this raising operation, the end of the teat screw 124 passes through the groove 126 formed on the rod 116, which has the effect of bringing the drop collecting plate 114 below the nippers 76 carrying the cap 16 as from the start of the rise thereof. This prevents any accidental dropping of a product droplet.

When the nippers 76 carrying the cap 16 arrives in the upper position, between said nippers and the jug 14, still held by the gripper 38, there is still an adequate distance to permit the bringing of the suction endpiece 138 between said two parts. The geared motor 152 of the sampling module 24 is then operated in order to bring the suction endpiece 138 into vertical alignment of the jug opening and closing module 22, which contains the jug 14 held by the gripper 38. This bringing into alignment of the suction endpiece 138 takes place when it has been brought into the upper position by the jack 146.

As soon as the suction endpiece 138 is positioned vertically of the jug 14, the jack 146 is actuated in order to lower the suction endpiece into the jug 14 held by the gripper 38. The suction of a given liquid quantity within the jug then takes place in a controlled manner using a not shown suction pump positioned outside the analysis unit.

Once sampling has taken place, the jack 146 is actuated in the opposite direction in order to draw the suction endpiece 138 out of the jug 14 and the geared motor 152 is operated so as to bring the endpiece 138 into its sampled liquid distribution position located vertically of the receptacle 26 in FIG. 1. The liquid sampled in the jug 14 can thus be introduced into one or more receptacles provided for this purpose, so that the desired analyses can take place.

As soon as the suction endpiece 138 is no longer in the alignment of the jug opening and closing module 22, the jack 86 can again be actuated so as to again lower the nippers 76 carrying the cap 16 and bring the latter into contact with the thread provided for receiving said cap on the jug 14. A rotation of the pin 74 is controlled in the screwing direction, in order to screw down the cap 16 again onto the jug 14. It is pointed out that the drop collecting plate 14 is automatically retracted when the nippers 76 carrying the cap 16 comes into the immediate vicinity of the jug 14.

When the cap has been screwed down again, the nippers 76 are released by an operation of the geared motor 100 and a further putting into operation of the jack 86 makes it possible to again raise the nippers 76 in order to then release the resealed jug 14.

The geared motor 60 can then be operated in order to bring the resealed jug to the right of the discharge station materialized by the lower chute 64 in FIG. 2. The base 44 is then retracted and the gripper 38 opens by an actuation of the jacks 42 and 48. The geared motors and jacks of the three modules 20, 22 and 24 are controlled by a not shown automaton.

The above description shows that the liquid sample taking assembly according to the invention makes it possible to obviate any unnecessary liquid and solid waste and ensures a particularly precise and effective control of the samples. Moreover, the automation of the different operations makes it possible to eliminate any error risk, as well as numerous tedious operations for the operators. It also eliminates any irradiation risk for the latter.

I claim:

1. Assembly for taking liquid samples from jugs sealed by screw caps comprising:
   a module for gripping the jugs, the gripping module having a gripper which in use grippingly holds a jug substantially in line with respect to a vertical axis of the jug;
   means for controlling opening and closing of the gripper;
   means for controlling horizontal displacement of the gripper between a jug gripping station and a jug opening station;
   a module for opening and closing the jugs, the opening and closing module including nippers, the nippers having a generally vertical axis, means for controlling tightening and loosening of the nippers, means for controlling rotation of the nippers, and means for controlling vertical displacement of the nippers; and
   a module for sampling liquid including a suction endpiece, the suction endpiece having a substantially vertical axis, means for controlling horizontal displacement of said endpiece between a sampling position, in which the vertical axes of the nippers and the suction endpiece coincide, and a position for distribution of a sampled liquid into a receptacle, and means for controlling vertical displacement of the suction endpiece.

2. Assembly according to claim 1, wherein the gripper is mounted at a lower end of a rotary shaft, said rotary shaft having a vertical axis which is displaced with respect to the axis of the jug held by said gripper, and wherein the means for controlling horizontal displacement of the gripper includes means for controlling rotation of said rotary shaft.

3. Assembly according to claim 1, wherein the gripping module also comprises a retractable base, said base being moveable to a position relatively below the gripper.

4. Assembly according to claim 1, wherein the gripping module comprises means for locking the gripper in position in front of the jug gripping station, and means for locking the gripper in position in front of the jug opening station.

5. Assembly according to claim 1, wherein the opening and closing module comprises a pin having a vertical axis and connecting the nippers to the rotation control means, and a rod positioned coaxially within the pin and connecting the nippers to the tightening and loosening control means.

6. Assembly according to claim 1, wherein the opening and closing module also comprises a retractable drop collecting plate, said plate being moveable to a position relatively below the nippers.

7. Assembly according to claim 6, wherein the means for controlling vertical displacement of the nippers acts simultaneously on the drop collecting plate, so that the plate is placed below the nippers when the nippers do not occupy a lower screwing and unscrewing position.

8. Assembly according to claim 1, wherein the suction endpiece is mounted on a horizontal arm, and rotation of the endpiece about a vertical axis displaced relative to the endpiece is controlled by the means for controlling horizontal displacement of the endpiece.

9. Assembly according to claim 1, wherein the suction endpiece is fluidly connected to a hydraulic safety guard.

10. Assembly according to claim 1, wherein the jug gripping station comprises an upper jug supply chute and a lower jug discharge chute, said chutes being coaxially aligned and spaced from one another and between which can be placed the gripper.

\* \* \* \* \*

UNITED STATES PATENT AND TRADEMARK OFFICE
CERTIFICATE OF CORRECTION

PATENT NO. : 5,533,407
DATED : July 9, 1996
INVENTOR(S) : Joseph Besnier

It is certified that error appears in the above-indentified patent and that said Letters Patent is hereby corrected as shown below:

Title page, item [54] and col. 1, the title should read "ASSEMBLY FOR TAKING LIQUID SAMPLES IN JUGS SEALED BY SCREW CAPS".

On the title page, in the abstract, line 6, delete "from" and insert --front--.

Column 1, lines 1 and 2, the title should read "ASSEMBLY FO TAKING LIQUID SAMPLES IN JUGS SEALED BY SCREW CAPS"; line 26, after "of" insert --:-- (colon); and line 26, after "jug" insert --, and--.

Column 2, line 25, delete "axes" and insert --axis--; and line 34, after "by" insert --the--.

Column 4, line 57, delete "driving" and insert --drawing--; and line 60, delete "analyzes" and insert --analysis--

Column 5, line 3, delete "axis,".

Column 6, line 10, after "station" insert --.-- (period); and line 38, after "and" delete --,-- (comma).

Signed and Sealed this

Thirty-first Day of December, 1996

Attest:

BRUCE LEHMAN

*Attesting Officer*          *Commissioner of Patents and Trademarks*